United States Patent [19]

Blass

[11] Patent Number: 5,220,932
[45] Date of Patent: Jun. 22, 1993

[54] DENTAL FLOSS AND METHOD OF MAKING IT

[75] Inventor: Jacob M. Blass, London, England

[73] Assignee: Westone Products Limited, London, England

[21] Appl. No.: 789,951

[22] Filed: Nov. 12, 1991

[30] Foreign Application Priority Data

| Dec. 20, 1990 | [GB] | United Kingdom | 9027594 |
| May 24, 1991 | [GB] | United Kingdom | 9111343 |
| Aug. 22, 1991 | [GB] | United Kingdom | 9118140 |

[51] Int. Cl.⁵ .................................................. A61C 15/00
[52] U.S. Cl. .................................................. 132/321
[58] Field of Search ............... 132/321, 322, 323, 324, 132/325, 326, 327, 200; 424/50

[56] References Cited

U.S. PATENT DOCUMENTS

| 3,699,979 | 10/1972 | Muhler et al. | 132/321 |
| 3,771,536 | 11/1973 | Dragan | 132/321 |
| 3,830,246 | 8/1974 | Gillings | 132/321 |
| 4,029,113 | 6/1977 | Guyton | 132/321 |
| 4,034,771 | 7/1977 | Guyton | 132/321 |
| 4,142,538 | 3/1979 | Thornton | 132/321 |
| 4,270,556 | 6/1981 | McAllister | 132/321 |
| 4,414,990 | 11/1983 | Yost | 132/321 |
| 4,776,358 | 10/1988 | Lorch | 132/321 |
| 4,836,226 | 6/1989 | Wolak | 132/321 |
| 4,996,056 | 2/1991 | Blass | 132/321 X |
| 4,998,978 | 3/1991 | Varum | 132/321 |
| 5,033,488 | 7/1991 | Curtis et al. | 132/321 |

Primary Examiner—Gene Mancene
Assistant Examiner—Nicholas D. Lucchesi
Attorney, Agent, or Firm—Larson and Taylor

[57] ABSTRACT

A dental floss comprises a monofilament ribbon of oriented non-porous PTFE having a tensile strength of at least 200 MPa, preferably 200–600 MPa, and a coating of wax. Optionally, the wax contains an additive. The wax is applied to the ribbon from a bath of molten wax to a lick roller, whose surface moves relatively to the ribbon at the contact region.

12 Claims, 1 Drawing Sheet

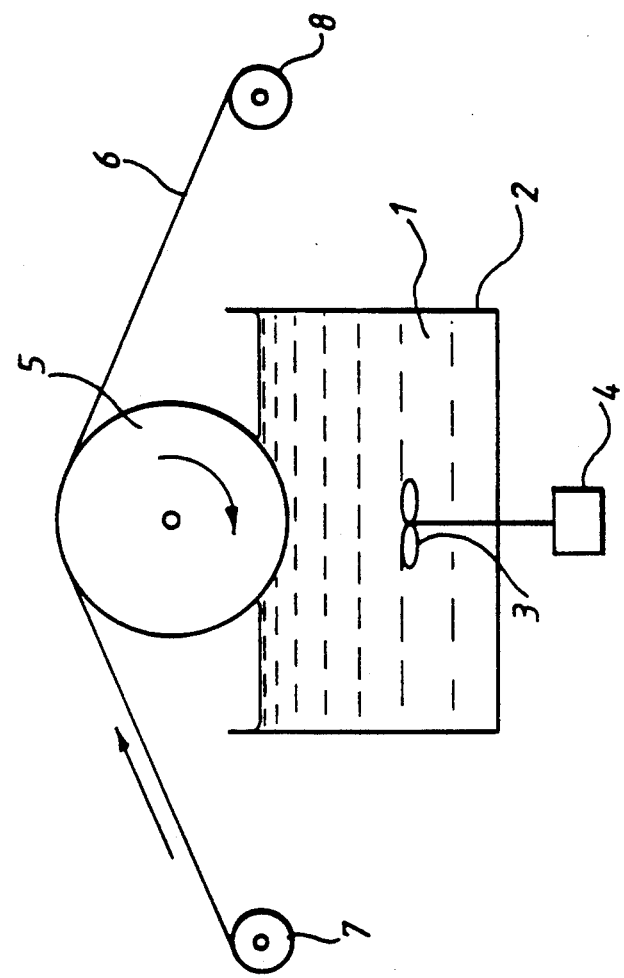

DENTAL FLOSS AND METHOD OF MAKING IT

BACKGROUND OF THE INVENTION

1. Field of the Invention

This invention relates to dental floss and a method of making it. By the term "dental floss" we mean both the product known as dental floss and the product known as dental tape. Indeed, the term "dental floss" is commonly used generically for both these. Dental tape is a floss of flattened cross-section.

2. Description of the Prior Art

It has recently become known to base a dental floss on expanded PTFE. This is disclosed in EP-A-335466, according to which the expanded PTFE has a polymeric matrix strength of at least 689.6 MPa and has an adhering coating of microcrystalline-wax.

SUMMARY OF THE INVENTION

The object of the present invention is to provide an improved dental floss, and also to provide a simple and effective manner of making it.

The present invention in one aspect is based on the realization that a satisfactory dental floss based on PTFE can be formed in a different manner from that described in EP-A-335466.

According to the present invention in one aspect there is provided a dental floss comprising a ribbon of oriented non-porous PTFE, having a tensile strength at least 200 MPa and a coating of wax thereon. Preferably the tensile strength of the PTFE is in the range 200–600 MPa. Preferably the PTFE is a monofilament ribbon, and preferably the width of the ribbon is in the range 0.5–4 mm, more preferably 1–3 mm, most preferably 1.2–2.4 mm. The thickness is preferably in the range 20–60 μm, more preferably 30–50 μm. The amount of wax is preferably in the range 5–30% by weight of the product.

By non-porous PTFE is meant substantially nonexpanded PTFE, i.e. PTFE having a density of at least 2 g/cm$^3$ (the theoretical density of solid PTFE is usually taken as 2.2). The PTFE may be uniaxially stretched, under conditions which do not cause expansion (i.e. it remains non-porous).

As usual, the term PTFE in this description and claims includes a range of fluoropolymers.

A wide variety of waxes may be employed. The wax chosen should be suitable and safe for oral use, and should be easily applied. The function of the wax is to stiffen the PTFE and give it a more pleasant 'feel'. The wax also acts to increase the frictional qualities, i.e. as an anti-lubricant.

With these considerations in mind, suitable waxes can be selected from natural waxes, from insects, animals or plants, petroleum waxes, e.g. microcrystalline waxes and synthetic waxes. Beeswax is especially preferred.

The use of beeswax has certain advantages. It is a natural product with no known adverse indications for human use, and therefore more acceptable, particularly in an article which is to be used in the mouth. It is readily available. It provides satisfactory coating characteristics and also friction characteristics in the use of the dental floss. It has been found to be especially applicable in the method of making the coated dental floss which is the second aspect of the present invention.

According to the invention in this second aspect, there is provided a method of making a wax-coated dental floss, optionally containing an additive, comprising applying the wax and optional additive from a bath of molten wax to a PTFE ribbon by means of a lick roller. In this aspect, the invention is applicable to both expanded and non-expanded PTFE. The preferred PTFE and the wax which may be used are already discussed above. Preferably the ribbon at the point of contact with the lick roller is moving relatively, to the contact surface of the roller. The lick roller may have a hard contact surface, e.g. of metal. Preferably, when the additive is employed, the wax bath is stirred, in order to achieve a uniform concentration of the additive.

The additive may be any suitable one for incorporation in a dental floss, i.e. suitable for release in the human mouth, and many are known. Examples are fluoride and polishing and abrasive agents.

BRIEF DESCRIPTION OF THE DRAWING

An embodiment of the invention will now be described by way of non-limitative example with reference to the accompanying drawing, in which the single figure is a diagrammatic view of a lick roller apparatus as used for the embodiment of the method of the present invention.

DESCRIPTION OF THE PREFERRED EMBODIMENT

In the drawing, there is shown a bath 1 of molten beeswax in a tank 2 stirred by rotating stirrer blade 3 driven by a motor 4. Dipping into the bath is a lick roller 5, whose surface is made of stainless steel. The depth to which the roller is immersed in the bath can be varied, and influences the amount of wax picked up by the roller, as does the relative speed of the surface of the roller. The diameter of the roller is 9 cm. In contact with the unimmersed top of the roller 5 is a ribbon 6 of expanded or non-expanded PTFE which is unwound from a coil 7 and rewound onto a coil 8 after having contacted the lick roller 5 over an angle of about 40°. This angle may be larger, e.g. up to 120°. The preferred range for the angular length of this contact is 30° to 120°. As shown, the direction of movement of the PTFE ribbon 6 is, at the contact point with the roller 5, in the same direction as the direction of the surface of the roller 5; this is preferred but is not necessary, provided that there is relative movement at the contact point. The wax cools to the solid state before the ribbon is rewound on the coil 8.

The bath 1 of beeswax is held typically at a temperature of 70° to 80° C. and contains an additive in particle form, whose concentration through the bath is maintained uniform by the stirrer 3. Thus the lick roller 5 picks up the wax with the additive and coats it onto both surfaces of the PTFE ribbon 6. The additive is distributed uniformly through the wax on the ribbon 6.

Uptake of wax (i.e. the amount deposited per unit length of ribbon 6) can be accurately controlled and varies in dependence on speed of the roller 5, relative speed of the roller 5 and the ribbon 6, the depth of the roller 5 in the bath, and the length of the contact region of the roller 5 and ribbon 6. The preferred ranges for these parameters are:

A. Circumferential speed of roller 5: 10 to 30 cm/s,
   and more particularly 14 to 20 cm/s
B. Relative speed of roller 5 and ribbon 6: 70 to 190 cm/s,
   and more particularly 100 to 150 cm/s C. Length of contact region of the roller 5 and ribbon 6:
3 cm to 12 cm,
and more particularly 3 to 7 cm.

To give one specific example, a uniaxially stretched PTFE ribbon of dimensions 1.5 mm ×0.045 mm, and a tensile strength of 510 MPa, a density of 2.089 g/cm$^3$ (i.e. a non-porous PTFE) was coated with beeswax and sodium fluoride powder (10% by weight in the wax) using the apparatus of the attached drawing. The beeswax was uniformly coated, by winding a pTFE ribbon at 1.43 m/s over a roller of diameter 9 cm rotating in the same direction as the direction of movement of the ribbon at 36 revolutions per minute (a circumferential speed of 17 cm/s). The length of the region of contact of the floss and roller was 7 cm. The additive was uniformly distributed through the coated beeswax. The uptake of beeswax on the PTFE ribbon was 15% by weight of the finished product.

This dental floss was found to be highly satisfactory in test use, and in particular can be inserted easily into the interdental regions, by virtue of the balanced frictional properties obtained with the combination of ribbon PTFE and wax.

The method achieves a highly uniform distribution of wax on the tape, and therefore a highly uniform amount of medicament or other additive per unit length. This is advantageous from a clinical point of view, to achieve desired delivery of the medicament on the mesial and distal surfaces of the teeth.

What is claimed is:

1. A dental floss comprising a monofilament ribbon of oriented uniaxially stretched non-porous PTFE having a tensile strength in the range 200–400 MPa and a coating of wax thereon, a width of said ribbon being in the range of 0.5–4 mm and a thickness of said ribbon in the range 20–60 μm.

2. A dental floss according to claim 1 wherein the width of said ribbon is in the range 1–3 mm.

3. A dental floss according to claim 1 wherein the amount of said wax is in the range 5–30% by weight of the total weight of the floss.

4. A dental floss according to claim 1 wherein said PTFE has a density of at least 2 g/cm$^3$.

5. A dental floss according to claim 1 wherein said wax is beeswax.

6. A method of making a wax-coated dental floss, comprising the steps of:
applying the wax from a bath of molten wax to a ribbon of PTFE by means of a lick roller, said applying step including the steps of immersing a first portion of a circumference of the lick roller in the bath, contacting a second portion of the circumference of the lick roller spaced from the first portion with the ribbon, and rotating the lick roller.

7. A method according to claim 6 wherein said PTFE is selected from expanded and non-expanded PTFE.

8. A method according to claim 6 wherein said contacting step of the ribbon at the second portion of the lick roller includes the step of moving the ribbon relative to the second contact portion of the lick roller.

9. A method according to claim 8 wherein said moving step moves said ribbon in the same direction as the rotation of said lick roller.

10. A method according to claim 6 wherein said lick roller has a hard contact surface.

11. A method according to claim 6 and further including the steps of adding an additive to the wax bath and stirring of said wax bath in order to achieve a uniform concentration of the additive therein.

12. A method according to claim 6 wherein said ribbon contacts said lick roller over an angular length of the circumference of said roller in the range 30° to 120°.

* * * * *